(12) United States Patent
Jarmon et al.

(10) Patent No.: US 8,756,791 B2
(45) Date of Patent: Jun. 24, 2014

(54) TAMPON APPLICATOR

(75) Inventors: George Jarmon, Camden/Wyoming, DE (US); Van Pham, Media, PA (US)

(73) Assignee: Eveready Battery Company, Inc., St. Louis, MO (US)

( * ) Notice: Subject to any disclaimer, the term of this patent is extended or adjusted under 35 U.S.C. 154(b) by 413 days.

(21) Appl. No.: 11/809,494

(22) Filed: Jun. 1, 2007

(65) Prior Publication Data

US 2007/0232982 A1 Oct. 4, 2007

Related U.S. Application Data

(60) Division of application No. 11/061,557, filed on Feb. 18, 2005, now abandoned, which is a continuation of application No. 10/271,201, filed on Oct. 15, 2002, now abandoned.

(60) Provisional application No. 60/330,105, filed on Oct. 17, 2001.

(51) Int. Cl.
*B22D 11/126* (2006.01)

(52) U.S. Cl.
USPC .......... 29/527.2; 29/527.1; 29/527.3; 29/458; 29/460; 604/15; 264/87

(58) Field of Classification Search
USPC .............. 29/527.1, 527.2, 527.3, 458, 460; 604/11–18, 57–60, 904; 264/39, 86, 264/87; 162/218–230, 382, 407
See application file for complete search history.

(56) References Cited

U.S. PATENT DOCUMENTS

| 3,419,005 A | 12/1968 | Lewing et al. ............... 128/263 |
| 3,697,631 A * | 10/1972 | Charman et al. ........... 264/37.19 |
| 3,935,363 A | 1/1976 | Burkholder et al. .......... 442/118 |
| 4,174,417 A | 11/1979 | Rydell .......................... 428/221 |
| 4,857,044 A | 8/1989 | Lennon ........................... 604/14 |
| 4,891,042 A | 1/1990 | Melvin et al. .................. 604/18 |
| 4,900,299 A | 2/1990 | Webb ............................. 604/11 |
| 5,279,541 A | 1/1994 | Frayman et al. ............... 604/14 |
| 5,300,358 A * | 4/1994 | Evers ........................... 442/396 |

(Continued)

FOREIGN PATENT DOCUMENTS

| BE | 437 937 | 2/1940 |
| GB | 2 166 656 | 5/1986 |

(Continued)

OTHER PUBLICATIONS

Fehrman Tool and Die Inc. http://www.ftdinc.com/moldmaint.htm (copyright 2000).*

(Continued)

*Primary Examiner* — Jermie Cozart
*Assistant Examiner* — Bayan Salone
(74) *Attorney, Agent, or Firm* — Energizer Personal Care, LLC

(57) ABSTRACT

A tampon applicator is provided having a barrel and/or a plunger molded from a pulp-based material. The barrel can be molded such that it includes a molded fingergrip area having a textured surface, at least one gripping structure, or any combination thereof. Petals may be molded on the pledget ejection end of the barrel. In addition, the exterior surface of the barrel is molded such that it is textured, smooth, or any combinations thereof. The molded tampon applicator exhibits superior flushability and compostability characteristics, without compromising the strength of the barrel or plunger.

10 Claims, 5 Drawing Sheets

(56) References Cited

U.S. PATENT DOCUMENTS

| | | | | |
|---|---|---|---|---|
| 5,328,568 A * | 7/1994 | Pregont | .................. | 162/226 |
| 5,346,468 A | 9/1994 | Campion et al. | .................. | 604/13 |
| 5,348,534 A | 9/1994 | Tomaszewski et al. | .................. | 604/14 |
| 5,350,354 A | 9/1994 | Billmers | | |
| 5,356,518 A | 10/1994 | Kelley et al. | .................. | 162/224 |
| 5,366,451 A | 11/1994 | Levesque | .................. | 604/378 |
| 5,389,067 A | 2/1995 | Rejai | .................. | 604/14 |
| 5,399,243 A * | 3/1995 | Miyamoto et al. | .................. | 162/274 |
| 5,431,784 A * | 7/1995 | Miyamoto et al. | .................. | 162/275 |
| 5,531,864 A * | 7/1996 | Miyamoto et al. | .................. | 162/199 |
| 5,547,544 A * | 8/1996 | Miyamoto et al. | .................. | 162/199 |
| 5,755,906 A | 5/1998 | Achter et al. | .................. | 156/217 |
| 5,800,377 A | 9/1998 | Campion et al. | .................. | 604/13 |
| 5,891,081 A | 4/1999 | McNelis et al. | .................. | 604/14 |
| 5,900,119 A * | 5/1999 | Goers et al. | .................. | 162/218 |
| 5,984,888 A | 11/1999 | Nielsen et al. | .................. | 604/12 |
| 6,083,447 A | 7/2000 | Turner | .................. | 264/401 |
| 6,126,782 A | 10/2000 | Liden et al. | .................. | 162/30.1 |
| 6,171,426 B1 | 1/2001 | Blanchard | .................. | 156/203 |
| 6,287,428 B1 * | 9/2001 | Gale et al. | .................. | 162/382 |
| 6,332,956 B1 * | 12/2001 | Lee et al. | .................. | 162/378 |
| 6,454,906 B1 * | 9/2002 | Nonomura et al. | .................. | 162/220 |
| 6,461,480 B1 * | 10/2002 | Otakura et al. | .................. | 162/220 |
| 6,468,398 B1 * | 10/2002 | Kumamoto et al. | .................. | 162/220 |
| 6,521,085 B2 * | 2/2003 | Kumamoto et al. | .................. | 162/130 |
| 6,547,931 B1 * | 4/2003 | Kumamoto et al. | .................. | 162/219 |
| 6,582,562 B2 * | 6/2003 | Gale et al. | .................. | 162/382 |
| 6,716,319 B2 * | 4/2004 | Gale et al. | .................. | 162/391 |
| 6,730,057 B2 * | 5/2004 | Zhao et al. | .................. | 604/11 |
| 7,727,208 B2 * | 6/2010 | Lemay et al. | .................. | 604/385.17 |
| 2001/0035275 A1 * | 11/2001 | Gale et al. | .................. | 162/382 |
| 2003/0040695 A1 * | 2/2003 | Zhao et al. | .................. | 604/15 |
| 2003/0051845 A1 * | 3/2003 | Gale et al. | .................. | 162/218 |
| 2003/0150583 A1 * | 8/2003 | Goto et al. | .................. | 162/218 |
| 2003/0209337 A1 * | 11/2003 | Nonomura | .................. | 162/218 |
| 2004/0054317 A1 * | 3/2004 | Lemay et al. | .................. | 604/15 |
| 2005/0150624 A1 * | 7/2005 | Toh et al. | .................. | 162/218 |
| 2005/0177091 A1 * | 8/2005 | Jarmon et al. | .................. | 604/15 |

FOREIGN PATENT DOCUMENTS

| | | | | |
|---|---|---|---|---|
| JP | 03-505055 | 11/1991 | | |
| JP | 06-19727 | 7/1994 | | |
| JP | 06-197927 | 7/1994 | .............. | A61F 13/20 |
| JP | 08-81897 | 3/1996 | .............. | A61F 13/26 |
| JP | 08-503151 | 4/1996 | | |
| JP | 2000-303400 | 10/2000 | | |
| JP | 2001-502929 | 3/2001 | | |
| JP | 2001-271299 | 10/2001 | | |
| WO | WO 97/01318 | 1/1997 | | |
| WO | WO 00/66213 | 11/2000 | | |

OTHER PUBLICATIONS

Wayback Machine Internet Archive (Apr. 2010).*
JP 2001-271299, Kao Corp, Feb. 10, 2001, Patent Abstracts of Japan, pp. 1-7.*
Japanese Office Action based on corresponding Japanese Application No. 2003-535689, dated Jan. 6, 2009.
Japanese Office Action based on corresponding Japanese Application No. 2003-535689, dated Jun. 27, 2008.
Canadian Office Action dated Dec. 7, 2009 for corresponding Canadian Patent Application No. 2,463,516.
Decision on Appeal from corresponding U.S. Appl. No. 10/271,201 dated May 12, 2009.
Korean Office Action dated Jul. 20, 2009 for corresponding Korean Application No. 10-2004-7005715 (with summarized translation).
Japanese Office Action based on corresponding Japanese Application No. 2003-535689, dated Apr. 1, 2010 (with English translation).
Canadian Office Action based on corresponding Canadian Application No. 2,463,516, dated Aug. 18, 2010.
Korean Office Action based on corresponding Korean Application No. 1020097021887, dated Oct. 6, 2010.
Supplementary European Search Report from corresponding European Application No. 02801730.9 dated Jul. 5, 2011.
Supplementary European Search Report dated Jul. 5, 2011 from corresponding European Application No. 0280173.9.
Canadian Office Action dated Mar. 14, 2011 from corresponding Canadian Application No. 2,463,516.
Canadian Office Action dated Mar. 14, 2011 for corresponding Canadian Patent Application No. 2,463,516.
*Australian examiner's first report for Patent Application No. 2002362842, Jul. 18, 2006.
*International Search Report dated Jan. 30, 2003 for International Application No. PCT/US02/32920.
*Written Opinion dated Nov. 4, 2003 for International Application No. PCT/US02/32920.
*International Preliminary Examination Report dated Jul. 7, 2004 for International Application No. PCT/US02/32920, Jul. 7, 2004.

* cited by examiner

TAMPON APPLICATOR

CROSS REFERENCE TO RELATED PATENT APPLICATIONS

This application is a divisional of U.S. patent application Ser. No. 11/061,557, filed on Feb. 18, 2005 entitled "Tampon Applicator," which is a continuation of U.S. patent application Ser. No. 10/271,201, filed on Oct. 15, 2002, which claims the benefit of U.S. Provisional Application No. 60/330,105, filed on Oct. 17, 2001. The aforementioned applications are herein incorporated by reference in their entirety.

BACKGROUND OF THE INVENTION

1. Field of the Invention

The present invention relates to an insertion device, such as a catamenial or tampon applicator. More particularly, the present invention relates to a tampon applicator formed from a molded pulp-based material.

2. Description of Related Art

The majority of tampon applicators on the market are manufactured from plastic, cardboard, or combinations of the two materials. Although preferred by some women because of a smooth and virtually frictionless exterior surface which enables easy, more comfortable insertion, plastic applicators have, at times, the perception of disposal problems. The plastic applicators can cause problems when flushed down a toilet, and instead should be disposed of with the dry trash. This method of disposal raises environmental concerns since most plastics are slow to biodegrade, and most are not compostable. Also, disposal in dry trash is not as discreet as flushing, which is a concern to many women.

On the other hand, paper applicators are flushable and exhibit good biodegradability features. The flushable feature is highly desired by most women because it provides a discreet way to dispose of the used applicator. The flushable feature also provides a sanitary aspect of quick and complete disposal. However, paper applicators are commonly thought of as less comfortable to insert, and are more difficult to form into shapes other than uniform cylindrical tubes. Many paper applicators are coated with a non-compostable coating to strengthen the applicator barrel and/or reduce the coefficient of friction of the barrel, rendering the applicator less environmentally friendly than consumers believe. Paper applicators also lack the advantage of plastic applicators of being able to be molded into more preferred, ergonomic and easier-to-use forms.

Therefore, there is a need for a tampon applicator that exhibits surfaces having smooth and virtually frictionless characteristics and molding versatility similar to plastic applicators while at the same time being flushable and compostable to at least the same degree of paper-based applicators. There is also a need for an applicator that is easy and cost efficient to manufacture.

SUMMARY OF THE INVENTION

It is an object of the present invention to provide a tampon applicator in which the barrel and/or plunger components are molded from pulp-based material.

It is another object of the present invention to provide such a tampon applicator in which the pulp-based material is a pulp slurry.

It is still another object of the present invention to provide such a tampon applicator with a barrel having a smooth interior and/or exterior surface with a low coefficient of friction.

It is yet another object of the present invention to provide such a tampon applicator in which both the barrel and the plunger are flushable and compostable.

It is a further object of the present invention to provide such a tampon applicator with a barrel having a fingergrip area molded directly on or in the exterior surface of the barrel.

It is still a further object of the present invention to provide such a tampon applicator with a barrel having a reduced diameter fingergrip area compared to the diameter of the barrel.

It is yet a further object of the present invention to provide such a tampon applicator having petals formed or molded on the ejection end of the barrel.

It is another object of the present invention to provide such a tampon applicator that has a barrel strength comparable to or superior to that of spiral wound and/or convolutely wound applicator barrels, despite being formed of less material.

It is still another object of the present invention to provide such a tampon applicator where the barrel and the plunger are molded from a process with production rates comparable to or superior to that of injection molding processes, resulting in a cost and time efficient process.

These and other objects and advantages of the present invention will be appreciated from a tampon applicator according to the present invention having a barrel and/or a plunger molded from a pulp-based material. The barrel can be molded such that it includes a molded fingergrip area having a textured surface, at least one gripping structure, or any combination thereof. To enhance the comfort to the user during insertion, petals may be molded on the insertion end of the barrel. In addition, the exterior surface of the barrel is molded such that it is textured, smooth, or any combination thereof. The molded tampon applicator exhibits superior flushability and compostability characteristics, without compromising the strength of either the barrel or plunger. The pulp-molding process used to mold the tampon applicator has a production rate comparable to or superior to that of an injection molding process, which results in an overall cost and time efficient process.

DETAILED DESCRIPTION OF THE INVENTION

Figure 1:
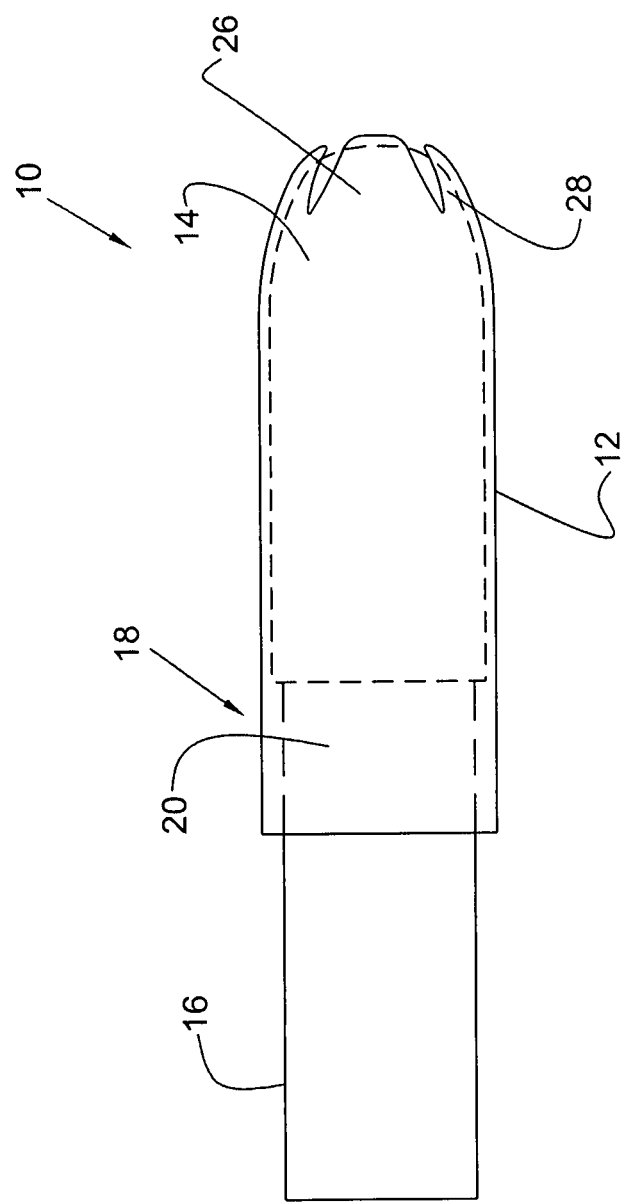
FIG. 1 is a plan view of a tampon applicator according to the present invention.

Referring to the drawings, and in particular FIG. 1, the tampon applicator of the present invention is represented generally by reference numeral 10. Tampon applicator 10 has a barrel 12 that can house a pledget 14 therein and a plunger 16 that can be connected to the barrel to engage, telescopically, the pledget housed in the barrel. Preferably, barrel 12 has a plunger receiving end or portion 18 and a fingergrip area 20 preferably adjacent end 18. According to the present invention, either barrel 12 and/or plunger 16 are made from a pulp-based material. Barrel 12 also has a pledget ejection portion or end 28. Ejection end 28 can be open-ended or have individual petals or connected, such as louvered together, petals. Preferably, end 28 has one or more individual petals 26. More preferably, end 28 has at least two petals 26. Petals 26 enclose pledget 14 upon insertion of applicator 10 into the vagina, resulting in user comfort. By including two or more petals 26, ejection forces are easily overcome.

In a more preferred embodiment of the present invention, both barrel 12 and plunger 16 are made from the pulp-based material. Also preferably, barrel 12 and/or plunger 16 are molded from this material. Barrel 12 and plunger 16 may be molded such that a substantially smooth surface results. A smooth outer surface corresponds to a reduced coefficient of friction, which ultimately facilitates insertion of applicator 10 into the vagina.

Thus, to further reduce friction, preferably both the outer surface of plunger 16 and the inner surface of barrel 12 are molded such that a substantially smooth surface is formed. The resulting reduction in friction between the plunger surface and the barrel surface, as well as between pledget 14 and the barrel's inner surface, allows the user to expel the pledget from barrel 12 with greater ease.

Additionally, any surface of barrel 12 and/or plunger 16 may be coated with any suitable material to enhance strength and/or reduce surface friction. Suitable coating materials include, for example, plastic, wax, silicone, epoxy, polyester, cellulose, lacquer, polyolefin, nylon, polyvinyl chloride, polyvinyl alcohol, nitrocellulose, cellophane, polylactide, or any combinations thereof.

The pulp-based material exhibits superior biodegradability and compostability, and can be molded to form both textured and non-textured surfaces. Suitable pulp-based material for molding barrel 12 and/or plunger 16 includes, for example, mechanical pulp, chemical pulp including sulfite, bisulfite, and sulfate types, thermo-mechanical pulp, chemi-thermo-mechanical pulp, recycle pulp including pre- and post-consumer types, synthetic pulp including polyethylene and polypropylene types, or any combinations thereof. These pulps may be bleached using, for example, chlorine based or chlorine-free systems, or non-bleached.

Mechanical pulp is made by placing a log, excluding the bark, through a grinding or refining process to separate the fibers. Generally, chemicals are not used in the process of making mechanical pulp.

Chemical pulp is typically made by a process that includes the use of a sulfur-based composition. Chips from de-barked logs are dissolved in a caustic composition containing a sulfur-based compound that is maintained under set heat and pressure conditions, thus forming a strong pulp.

Thermo-mechanical pulp and chemi-thermo-mechanical pulp are formed by a combination of the mechanical and chemical processes described above. Generally, with both types of pulp, de-barked logs are chipped and then heated to temperatures that soften the chips before being passed through a grinding process. With the chemi-thermo-mechanical pulp, chemicals are sprayed onto the chips, in addition to the above-described process, to reduce the undesirable effects of the retained natural wood substances.

Additionally, the pulp-based material may contain one or more additional components typically used in papermaking, such as, for example, one or more fillers, binding agents, or combinations thereof. Suitable fillers include, for example, calcium carbonate, clay, or any mixtures thereof. Suitable binding agents include, for example, starch, melamine resins, or any combinations thereof.

The cellulosic-based pulps may be derived, for example, from hardwood, softwood, cotton, straw, flax, or any combinations thereof. Preferably, the pulp-based material is a non-chlorine bleached softwood sulfate pulp.

It has been found that synthetic pulps can act as heat activated adhesives. Therefore, their inclusion in the pulp mix results in a molded applicator that can be heat stabilized to various degrees, depending on the amount of synthetic pulp provided in the pulp mix and the temperature/pressure profile applied to the molded applicator.

By molding the components of the tampon applicator 10 with a pulp-based material, various textures can be imparted on the outer surface of barrel 12 and/or plunger 16. Moreover, the texture can be varied on any single applicator component so as to form, for example, fingergrip area 20 on only a portion of barrel 12, while forming a smooth surface on the remaining portion of the barrel.

Figure 2:
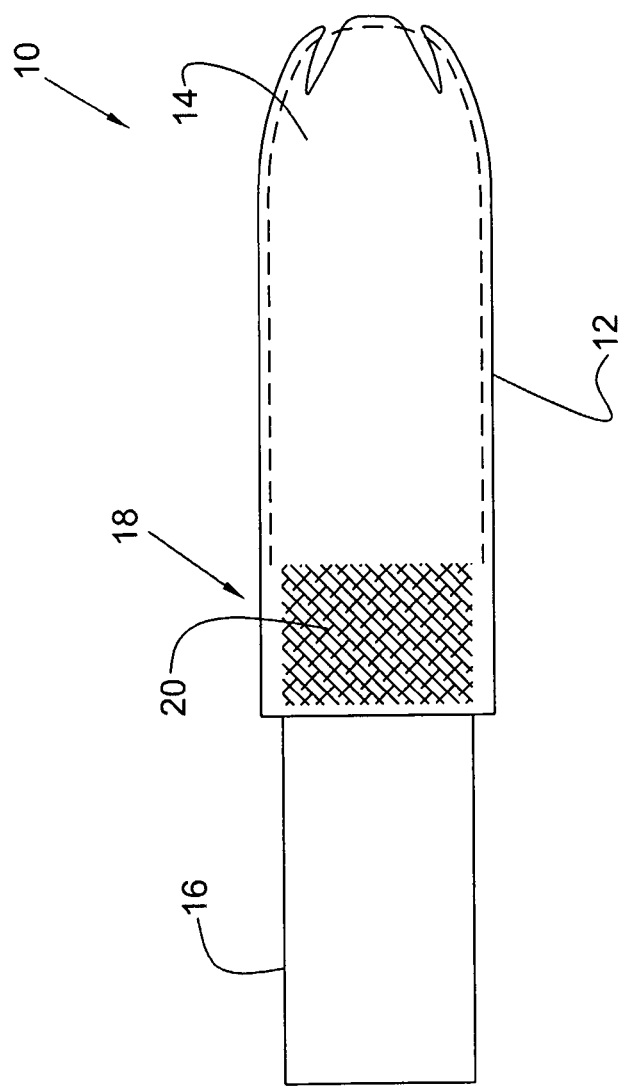
FIG. 2 is a plan view of a tampon applicator having a textured fingergrip area according to a first preferred embodiment of the present invention.

Referring to FIG. 2, plunger end or portion 18 may be molded such that a textured fingergrip area 20 is formed. The texture imparted on or in the outer surface of fingergrip area 20 provides an increased grippability to barrel 12. Due to the pulp-based material that forms barrel 12, any texture suitable for increasing the grippability of the barrel may be imparted on the outer surface of fingergrip area 20.

Figure 3:
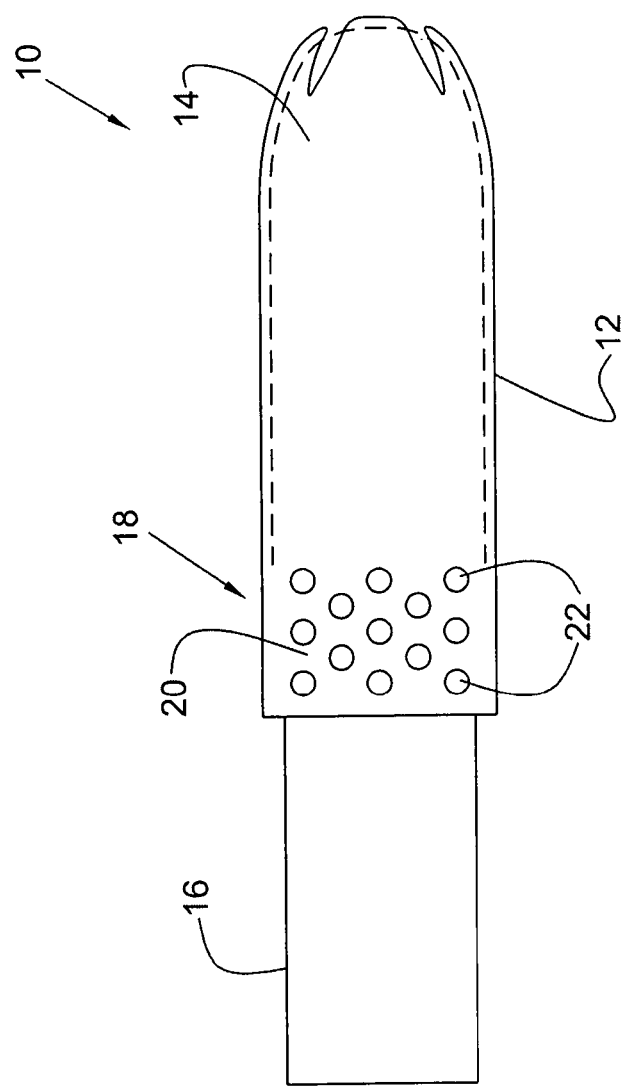
FIG. 3 is a plan view of a tampon applicator having gripping structures according to a second preferred embodiment of the present invention.

Referring to FIG. 3, the grippability of fingergrip area 20 may be enhanced by forming at least one gripping structure 22, and preferably a plurality of gripping structures 22, into the outer surface of the fingergrip area. Preferably, gripping structures 22 are molded into fingergrip area 20 by the same molding process used to form barrel 12. Fingergrip area 20 may be textured, as described above with respect to FIG. 2, in addition to having at least one gripping structure 22.

Gripping structures 22 may be molded or formed in any number and/or configuration suitable for creating enhanced grippability on barrel 12 or applicator 10. The gripping structures 22 may be molded such that they extend above the outer surface of fingergrip area 20, they extend below the outer surface of the fingergrip area, the tip or upper edge of the gripping structure is aligned with the outer surface of the fingergrip area, or any combinations thereof. Suitable shapes or configurations for gripping structures 22 include, for example, one or more squares, circles, ovals, diamonds, triangles, rectangles, polygons, arcs, cones, lines, ribs, treads, slits, grooves, protuberances, louvers, or any combinations thereof.

Figure 4:
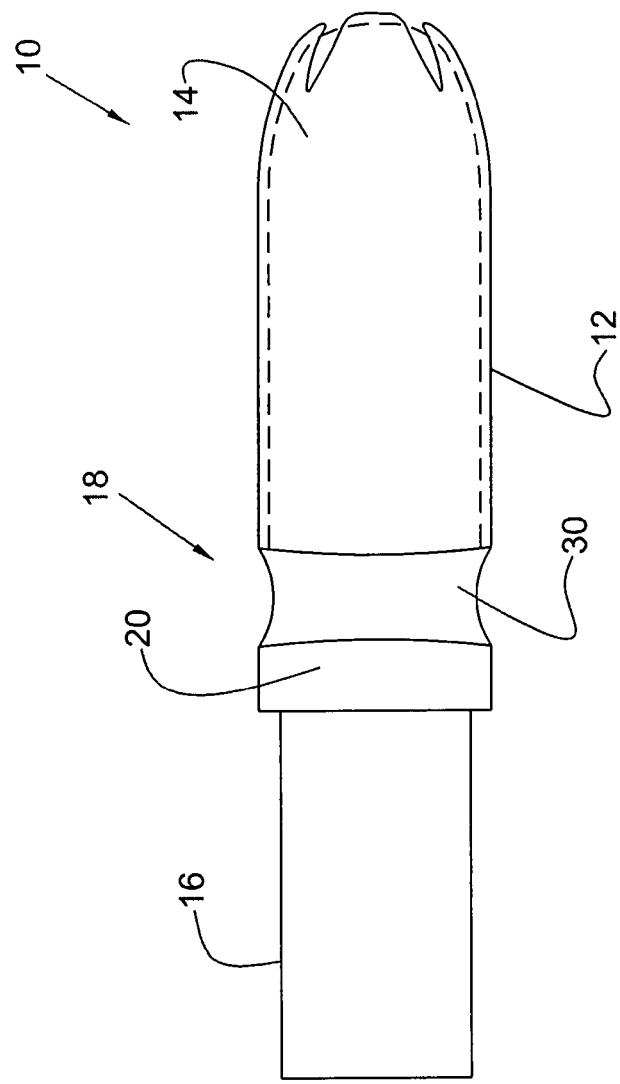
FIG. 4 is a plan view of a tampon applicator having a concave fingergrip according to a third preferred embodiment of the present invention.

Referring to FIG. 4, fingergrip area 20 can be molded such that a circumferentially disposed concavity 30 is formed, resulting in a superior fingerhold area. The resulting concave fingerhold provides increased grippability of applicator 10.

Figure 5:
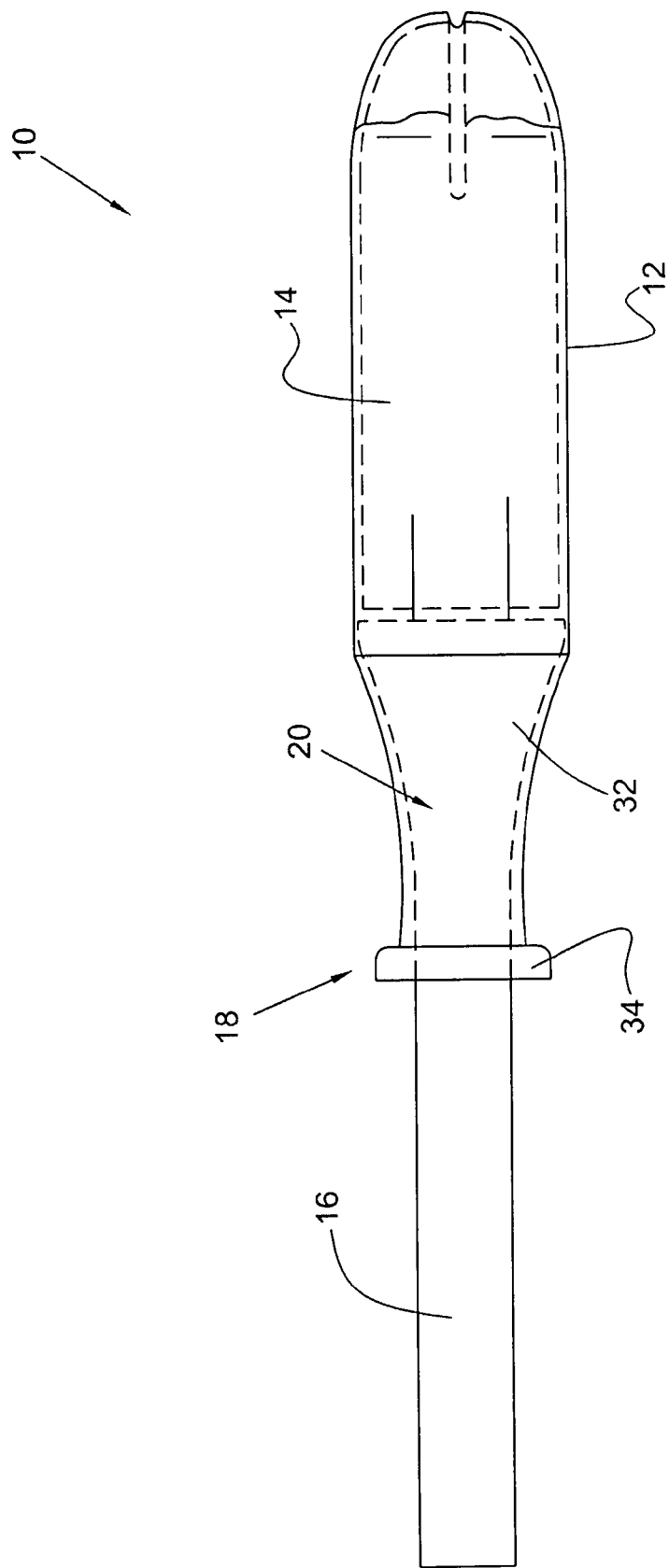
FIG. 5 is a plan view of a tampon applicator having a tapered fingergrip according to a fourth preferred embodiment of the present invention.

Referring to FIG. 5, fingergrip area 20 can be molded such that a tapered, reduced cross-sectional area fingergrip 32 is formed, resulting in a superior fingerhold area. In addition, a circumferential ring 34 may also be molded at end 18 to further provide an enhanced fingerhold area.

To form tampon applicator 10 from molded pulp-based material, barrel 12 is molded from the pulp-based material. To further enhance insertion comfort of the tampon applicator user, petals 26 may be formed, or molded into or on ejection end 28 of barrel 12. Petals 26 may be molded such that they are formed in an open position and later re-shaped to form an enclosed insertion tip. This allows top-loading of an absorbent pledget into barrel 12. Alternatively, petals 26 may be molded such that they are in the closed position, thus avoiding the need for further forming or shaping of the petals.

As stated above, plunger 16 may also be molded from the pulp-based material. Pledget 14 is loaded into the molded barrel 12, and plunger 16 is inserted or connected to the barrel. To enhance the grippability of tampon applicator 10, during the molding process, fingergrip area 20 has a texture, at least one gripping structure, or any combination thereof, may be molded to or formed in or on the outer surface of barrel 12. The fingergrip area 20 may be molded when initially molding barrel 12 or any time subsequent thereto, even after assembly of applicator 10 (with or without pledget 14).

Generally, by way of example, the pulp-molding process is done on a pulp machine having a pulp end and a press end. At the pulp end of the machine, the raw material is placed in a mixing vessel where it is agitated until a pulp slurry is formed. The pulp slurry material is then transferred to a pulp slurry bath. A screened tool having a plurality of molds shaped in the desired applicator component to be molded, is provided. A vacuum is drawn on the screened tool and it is dipped into the pulp slurry bath. The pulp slurry is drawn by the vacuum onto the surface of the screened tool. While maintaining the vacuum, the screened tool is removed from the pulp slurry bath and resurfaces with rough pulp molded components. The screened tool is then spray washed to remove excess pulp from the areas on the screened tool that don't have a vacuum.

Once cleaned, the screened tool is transferred to a press at the press end of the pulp machine where the molded pulp on the screened tool is compressed, while applying heat, to compress, densify, and smooth the molded pulp. The vacuum is discontinued and the molded pulp is then removed from the screened tool as a finished product.

The pulp-molding process used to form the tampon applicator of the present invention has been found to be extremely cost and time efficient. Production rates comparable to and/or superior to existing injection molding process rates are achievable with the pulp-molding process. In addition, as a result of the pulp-molding process, it is believed that the resulting pulp-molded barrel strength is comparable to and/or superior to that of a spiral wound applicator barrel and stronger than a convolutely wound applicator barrel. This strength is achieved while using fewer raw materials to form the molded barrel than are used to form a spiral wound barrel, resulting in significant cost savings. Finally, the pulp-molding process achieves superior production and cost efficiencies because the same molding equipment can be used to form any component of the applicator of the present invention, only requiring that the screen and compression tooling be changed accordingly.

It should be noted that the pulp-molding materials and processes set forth above for the present invention are equally applicable for use in making a tampon applicator formed from multiple, discrete components.

The foregoing specification and drawings are merely illustrative of the present invention and are not intended to limit the invention to the disclosed embodiments. Variations and changes, which are obvious to one skilled in the art are intended to be within the scope and nature of the present invention, which is defined in the appended claims.

What is claimed is:

1. A method for forming a tampon applicator comprising the steps of:
    providing a screened tool having a mold, said mold having a complementary shape to a barrel of the tampon applicator;
    agitating a pulp based material into a pulp based material slurry;
    dipping said screened tool into said slurry to place said pulp based material onto a surface of said screened tool by vacuum drawing said slurry onto said surface of said screened tool, wherein said pulp based material is selected from the group consisting of mechanical pulp, chemical pulp, thermo-mechanical pulp, chemi-thermo-mechanical pulp, and any combinations thereof, and wherein said screened tool forces said pulp based material into a shape complementary to said barrel;
    washing an excess of said pulp based material from said screened tool;
    after washing, solidifying said barrel on said screened tool, wherein the solidifying of said barrel results in said barrel having an outer surface that is suitable to facilitate vaginal insertion; and
    connecting said barrel to a second tampon applicator component to form the tampon applicator.

2. The method of claim 1, wherein said solidified barrel has a coefficient of friction complementary for insertion to a vagina.

3. The method of claim 1, wherein said second tampon applicator component is a thermoplastic tampon applicator component.

4. The method of claim 1, wherein said second tampon applicator component is selected from the group consisting of a non-molded plunger, a non-molded barrel, a pledget, and any combinations thereof.

5. The method of claim 1, wherein said barrel has a finger grip area, and wherein said finger grip area is molded into said outer surface.

6. The method of claim 1, wherein said barrel has a finger grip area, and wherein said finger grip area has at least one gripping structure.

7. The method of claim 6, wherein said at least one gripping structure is selected from the group consisting of one or more squares, circles, ovals, diamonds, triangles, rectangles, polygons, arcs, cones, lines, ribs, treads, slits, grooves, protuberances, louvers, and any combinations thereof.

8. The method of claim 1, further comprising the step of molding a petal on said barrel.

9. The method of claim 1, further comprising the step of applying a coating material to a surface of said barrel or said second tampon applicator component, wherein said coating material is selected from the group consisting of plastic, wax, silicone, epoxy, polyester, cellulose, lacquer, polyolefin, nylon, polyvinyl chloride, polyvinyl alcohol, nitrocellulose, cellophane, polylactide, and any combinations thereof.

10. A method for forming a tampon applicator comprising the steps of:
    providing a mold, said mold having a complementary shape to one or more components of the tampon applicator;
    providing a raw pulp based material, wherein said raw pulp based material is selected from the group consisting of mechanical pulp, chemical pulp, thermo-mechanical pulp, chemi-thermo-mechanical pulp, and any combinations thereof;
    agitating said raw pulp based material into a pulp based material slurry;
    drawing said pulp based material slurry onto said mold, said drawing forcing said slurry to have a shape that is complementary to said one or more components;
    solidifying said pulp based material slurry on said mold, said solidifying comprising compressing said slurry on said mold while heat is applied; and
    removing said one or more components from said mold.

* * * * *